US009994469B2

(12) United States Patent
Taguchi et al.

(10) Patent No.: US 9,994,469 B2
(45) Date of Patent: Jun. 12, 2018

(54) WASTEWATER TREATMENT PROCESS (71) Applicant: FUJI ELECTRIC CO., LTD., Kawasaki-shi, Kanagawa (JP)

(72) Inventors: Kazuyuki Taguchi, Hamura (JP); Keigo Yasuda, Kawasaki (JP); Yosuke Hanai, Tokyo (JP); Tetsuya Abe, Kawasaki (JP); Hideharu Mae, Saitama (JP)

(73) Assignee: FUJI ELECTRIC CO., LTD., Kawasaki-shi, Kanagawa (JP)

(*) Notice: Subject to any disclaimer, the term of this patent is extended or adjusted under 35 U.S.C. 154(b) by 0 days. days.

(21) Appl. No.: 15/116,054

(22) PCT Filed: Feb. 3, 2015

(86) PCT No.: PCT/JP2015/052947
§ 371 (c)(1),
(2) Date: Aug. 2, 2016

(87) PCT Pub. No.: WO2015/119100
PCT Pub. Date: Aug. 13, 2015

(65) Prior Publication Data
US 2017/0166465 A1 Jun. 15, 2017

(30) Foreign Application Priority Data
Feb. 4, 2014 (JP) .................. 2014-019101

(51) Int. Cl.
C02F 3/34 (2006.01)
C02F 3/30 (2006.01)
(Continued)

(52) U.S. Cl.
CPC .............. C02F 3/34 (2013.01); C02F 3/302 (2013.01); C12N 1/20 (2013.01); C12R 1/07 (2013.01);
(Continued)

(58) Field of Classification Search
CPC ...... C02F 3/34; C02F 3/302; C02F 2101/163; C02F 2305/06; C12R 1/07; C12R 1/20; C12R 1/125
(Continued)

(56) References Cited

U.S. PATENT DOCUMENTS 6,767,464 B2 7/2004 Boyd et al.
9,297,114 B2 3/2016 Bianchi et al.

FOREIGN PATENT DOCUMENTS

CN 102465102 A 5/2012
EP 2565166 A1 3/2013
(Continued)

OTHER PUBLICATIONS

Machine-generated English Translation of JP 2009-131773, retrieved on Sep. 12, 2017.*
(Continued)

Primary Examiner — Fred Prince
(74) Attorney, Agent, or Firm — Holtz, Holtz & Volek PC (57) ABSTRACT Provided is a wastewater treatment method that keeps *Bacillus* predominant inside the biological treatment tank and makes it possible to improve the water quality of the treated water while suppressing the volume of sludge generated in association with wastewater treatment. A wastewater treatment method for purifying wastewater by microorganisms in a biological treatment tank wherein the wastewater is purified by causing a first microorganism belonging to the genus *Bacillus* that is + for nitric acid reduction and − for starch decomposition and a second microorganism that is − for nitric acid reduction and + for starch decomposition in testing of the physiological properties of microorganisms to be predominant inside the biological treatment tank.

7 Claims, 8 Drawing Sheets (51) Int. Cl.
*C12N 1/20* (2006.01)
*C12R 1/07* (2006.01)
*C12R 1/125* (2006.01)
*C02F 101/16* (2006.01)

(52) U.S. Cl.
CPC ........ *C12R 1/125* (2013.01); *C02F 2101/163* (2013.01); *C02F 2305/06* (2013.01)

(58) Field of Classification Search
USPC ............... 210/605, 610, 611, 630, 903, 905; 435/252.5
See application file for complete search history.

(56) References Cited

FOREIGN PATENT DOCUMENTS

| | | | |
|---|---|---|---|
| JP | 2001162297 | A | 6/2001 |
| JP | 2001286884 | A | 10/2001 |
| JP | 2002113486 | A | 4/2002 |
| JP | 2002263686 | A | 9/2002 |
| JP | 2004344886 | A | 12/2004 |
| JP | 2005295887 | A | 10/2005 |
| JP | 2005329301 | A | 12/2005 |
| JP | 2007105630 | A | 4/2007 |
| JP | 2008018357 | A | 1/2008 |
| JP | 2009131773 | A | 6/2009 |
| JP | 2009142786 | A | 7/2009 |
| JP | 2010155189 | A | 7/2010 |
| WO | 03051485 | A1 | 6/2003 |
| WO | 2007054114 | A1 | 5/2007 |
| WO | 2013137010 | A1 | 9/2013 |

OTHER PUBLICATIONS

International Search Report (ISR) dated Mar. 17, 2015 issued in International Application No. PCT/JP2015/052947.
Madhaiyan, et al., "*Bacillus methylotrophicus* sp. nov., a methanol-utilizing, plant-growth-promoting bacterium isolated from rice rhizosphere soil", International Journal of Systematic and Evolutionary Microbiology, 2010, vol. 60, No. 10, pp. 2490-2495.
Extended European Search Report (EESR) dated Aug. 25, 2017 which issued in counterpart European Application No. 15746742.4.
"Bacillus amyloliquefaciens strain IrB12 16S ribosomal RNA gene, partial sequence", ncbi search for KY404010, found in sequence identity search with SEQ ID 1, <https://www.ncbi.nlm.nih.gov/nuccore/FJ434645>, retrieved on Mar. 13, 2018.
"Bacillus subtilis strain GZUB15 16S ribosomal RNA gene, partial sequence", ncbi search for FJ434645, found in sequence identity search with SEQ ID 1, <https://www.ncbi.nlm.nih.gov/nuccore/KY404010>, retrieved on Mar. 13, 2018.
European Office Action dated Mar. 22, 2018 issued in counterpart European Application No. 15746742.4.
Dunlap, et al., "Bacillus velezensis is not a later heterotypic synonym of Bacillus amyloliquefaciens; Bacillus methylotophicus, Bacillus amyloliquefaciens supsp.plantarum and 'Bacillus oryzicola' are later heterotypic synonyms of Bacillus velzensis based on phylogenomics", International Journal of Systematic and Evolutionary Microbiology, vol. 66, No. 3, Mar. 1, 2016, pp. 1212-1217.

\* cited by examiner

WASTEWATER TREATMENT PROCESS

TECHNICAL FIELD

The present invention relates to a wastewater treatment method for biodegrading wastewater containing organic matter, such as household wastewater or industrial wastewater, to water quality that meets wastewater standards.

BACKGROUND ART

Biological treatment such as the conventional activated sludge process or oxidation ditch process is an extremely advantageous treatment method in terms of cost in wastewater treatment because it does not require as complex equipment as methods of chemical and physical purification, generates few byproducts, and also takes less energy input. The conventional activated sludge process in particular is widely used in economically developing emerging countries because it can treat large quantities of wastewater in a short time and is relatively easy to control.

Broadly speaking, a conventional activated sludge process system consists of an aeration tank (biological treatment tank) and a settling tank. Aerobic conditions are produced in the aeration tank by blowing air into the wastewater by a blower. Microorganisms that purify organic matter are activated, and the organic matter in the wastewater is removed. The activated sludge and treated water are separated in the settling tank. The treated water of the upper layer is then removed to the outside, and released into the environment after appropriate post-treatment. The activated sludge, on the other hand, is sent back to the aeration tank to maintain the necessary microbial concentration in the aeration tank, and any excess (excess sludge) is removed to the outside and finally disposed of as industrial waste. The microorganisms in the aeration tank are the major component of the excess sludge which is a conglomerate of microorganisms that have grown using the organic matter in the wastewater as a substrate. Therefore, the volume of sludge generated also increases as the organic matter in the wastewater is removed.

On the other hand, the microorganisms utilized in such biological treatment naturally become predominant or are activated in the wastewater treatment environment. The food chain also stretches from bacteria to protozoa, and the organic matter is removed. Removal of the organic matter in wastewater therefore takes a relatively long time in biological treatment.

Improvement of the wastewater treatment speed using a method of making *Bacillus*, which have a rapid growth rate even among the microorganisms in the wastewater treatment environment and produce large amounts of enzymes to decompose organic matter, predominant has therefore been proposed and put to practical use. For example, the following Patent Documents 1-6 propose making *Bacillus* predominant in the aeration tank and conducting wastewater treatment. The following Patent Documents 7-13 also propose making *Bacillus* predominant and adding minerals including silicon to maintain them.

PRIOR ART DOCUMENTS

Patent Documents

[Patent Document 1] Japanese Laid-Open Patent Application No. 2010-155189
[Patent Document 2] Japanese Laid-Open Patent Application No. 2009-142786
[Patent Document 3] Japanese Laid-Open Patent Application No. 2009-131773
[Patent Document 4] Japanese Laid-Open Patent Application No. 2009-142786
[Patent Document 5] Japanese Laid-Open Patent Application No. 2008-18357
[Patent Document 6] Japanese Laid-Open Patent Application No. 2007-105630
[Patent Document 7] Japanese Laid-Open Patent Application No. 2005-329301
[Patent Document 8] Japanese Laid-Open Patent Application No. 2005-295887
[Patent Document 9] Japanese Laid-Open Patent Application No. 2004-344886
[Patent Document 10] Japanese Laid-Open Patent Application No. 2002-263686
[Patent Document 11] Japanese Laid-Open Patent Application No. 2002-113486
[Patent Document 12] Japanese Laid-Open Patent Application No. 2001-286884
[Patent Document 13] Japanese Laid-Open Patent Application No. 2001-162297

DISCLOSURE OF THE INVENTION

Problems to be Solved by the Invention

However, in biological treatment, the problem is that the excess sludge produced increases as the organic matter in the wastewater is assimilated by the microorganisms, raising the sludge treatment cost. This is also true when using *Bacillus*.

Additionally, in biological treatment, a nitrogen component in excess of wastewater standards sometimes remains in the treated water since the capacity to remove the carbon component in the organic matter is generally high, but the nitrogen and phosphorus removal capacity is low. Such instances necessitated adding ancillary equipment comprising a nitrogen removal step by a physicochemical means such as ion-exchange, reverse osmosis membrane filtration, ammonia stripping, or the like to the final stage of biological treatment. Alternatively, it was necessary to adjust the treatment conditions to utilize microorganisms having high nitrification-denitrification ability as a biological process. These measures make the system more complex and less efficient, together with raising the treatment cost.

Therefore, it is an object of the present invention is to provide a wastewater treatment method that keeps *Bacillus* predominant in the biological treatment tank and makes it possible to improve the water quality of the treated water while suppressing the volume of sludge generated in association with wastewater treatment.

Means to Solve the Problems

To achieve the aforesaid objective, the wastewater treatment method of the present invention is a wastewater treatment method for purifying wastewater by microorganisms in a biological treatment tank wherein the wastewater is purified by making a first microorganism belonging to the genus *Bacillus* that is + for nitric acid reduction and – for starch decomposition and a second microorganism belonging to the genus *Bacillus* that is – for nitric acid reduction and + for starch decomposition in testing of the physiological properties of microorganisms predominant in the biological treatment tank.

In the wastewater treatment method of the present invention, the first microorganism is preferably a microorganism belonging to *Bacillus methylotrophicus*.

In addition, the second microorganism is preferably a microorganism belonging to *Bacillus subtilis*.

In addition, the first microorganism is preferably a microorganism having a 16S rDNA sequence of SEQ ID NO: 1.

In addition, the second microorganism is preferably a microorganism having a 16S rDNA sequence of SEQ ID NO: 2.

In addition, the first microorganism is preferably *Bacillus methylotrophicus* FET-008 (accession no.: NITE BP-1426) belonging to the genus *Bacillus*.

In addition, the second microorganism is preferably *Bacillus* sp. FET-037 (accession no.: NITE BP-1427) belonging to the genus *Bacillus*.

In addition, the first microorganism and the second microorganism are preferably made predominant in the biological treatment tank by adding minerals including silicic acid.

The present invention also provides *Bacillus methylotrophicus* FET-008 (accession no.: NITE BP-1426) belonging to the genus *Bacillus*.

The present invention also provides *Bacillus* sp. FET-037 (accession no.: NITE BP-1427) belonging to the genus *Bacillus*.

Advantageous Effects of the Invention

The wastewater treatment method of the present invention makes it possible to improve the water quality of the treated water by removing the nitrogen in the wastewater while suppressing the volume of sludge generated in association with wastewater treatment because it causes wastewater to be purified by making predominant in the biological treatment tank a first microorganism belonging to the genus *Bacillus* that is + for nitric acid reduction and − for starch decomposition and a second microorganism that is − for nitric acid reduction and + for starch decomposition in testing of the physiological properties of microorganisms.

BEST MODE FOR CARRYING OUT THE INVENTION

The wastewater to be treated by the present invention is not particularly restricted as long as the wastewater contains nitrogen and organic matter. Examples include household wastewater and wastewater from the cereal starch production industry, dairy products production industry, meat centers, sugar production industry, livestock food products production industry, livestock farming, meat products production industry, meat ham and sausage production industry, fishery paste product production industry, fishery food products production industry, organic chemical industry production industry, inorganic chemical industry production industry, and the like.

As for the microorganisms used in the present invention, a microorganism belonging to the genus *Bacillus* that is + for nitric acid reduction and − for starch decomposition in testing of the physiological properties of microorganism is used as a first microorganism. A microorganism belonging to the genus *Bacillus* that is − for nitric acid reduction and + for starch decomposition in testing of the physiological properties of microorganism is also used as a second microorganism.

Here, testing of the physiological properties can be performed, for example, as follows in accordance with the usual method (refer to Experimental Agricultural Chemistry, the first volume, University of Tokyo Department of Agricultural Chemistry, published 1974, p. 240, p. 242).

(1) Nitric Acid Reduction

Several tubes of peptone water containing 0.1% potassium nitrate, 0.3% meat extract, and 0.5% peptone are inoculated with bacteria and cultured. Each is removed after 1, 2, 3, and 5 days, and 1 mL each of the following solution A and solution B is added and mixed thoroughly. If the culture broth turns red within 30 minutes, this shows the presence of nitrous acid (having the ability to reduce nitric acid).

Solution A: 0.5 g of α-naphthylamine dissolved by warming in 100 mL of 5 N acetic acid.

Solution B: 0.8 g of sulfanilic acid dissolved by warming in 100 mL of 5 N acetic acid.

(2) Starch Decomposition

Bacteria are inoculated in a line on slabs of agar medium containing soluble starch in a concentration of 0.2-1.0% and cultured. Iodine solution is poured onto the slab after the bacteria have grown. If a clear band that does not turn blue forms around the colonies of bacteria, this shows starch decomposition (having the ability to decompose starch).

Specifically, *Bacillus methylotrophicus* FET-008 (accession no.: NITE BP-1426) belonging to the genus *Bacillus*, isolated by the present inventors from sludge from biological wastewater treatment, can be used as the first microorganism. This strain is referred to hereinafter as "FET-008." In addition to this, *Bacillus methylotrophicus* CBMB205T (EU 194897) and the like can also be used.

In addition, *Bacillus* sp. FET-037 (accession no.: NITE BP-1427) belonging to the genus *Bacillus*, isolated by the present inventors from sludge from biological wastewater treatment, can be used as the second microorganism. This strain is referred to hereinafter as "FET-037." In addition to this, *Bacillus subtilis* subsp. *subtilis* DSM 10T (AJ 276351), *Bacillus subtilis* subsp. *subtilis* NBRC 3009, *Bacillus subtilis* subsp. *subtilis* ATCC 6051, and the like can also be used.

The bacteriological properties of FET-008 are shown below.

A. Morphological Properties
  (1) Cell size: 1.7×0.7 μm
  (2) Cell shape: rod
  (3) Motility: −
  (4) Spores: +
B. Culture Properties
  (1) Nutrient agar medium
    (a) Colony color: milky white
    (b) Colony morphology: not shiny, rough perimeter
  (2) Nutrient gelatin medium: liquefaction
  (3) Litmus milk medium: acid production, liquefaction
  (4) Growth temperature
    (a) 30° C.: +
    (b) 60° C.: −
C. Physiological Properties
  (1) Gram staining: +
  (2) Aerobic or anaerobic
    (a) Aerobic
    (b) Growth under anaerobic conditions: −
  (3) Nitrate reduction: +
  (4) MR test: −
  (5) VP test: +
  (6) Production of hydrogen sulfide: −
  (7) Utilization of citric acid: −
  (8) Pigment production: −
  (9) Urease activity: +
  (10) Oxidase activity: −
  (11) Catalase activity: +
  (12) OF test: glucose non-decomposing bacterium
  (13) Properties by "Api 50 CHB" (trade name, Sysmex Co., Ltd.)
    (a) L-arabinose: +
    (b) D-xylose: +
    (c) D-glucose: +
    (d) D-mannose: +
    (e) D-fructose: +
    (f) D-galactose: −
    (g) Maltose: +
    (h) Sucrose: +
    (i) Lactose: +
    (j) Trehalose: +
    (k) D-sorbitol: +
    (l) D-mannitol: +
    (m) Inositol: +
    (n) Glycerol: +
    (o) Starch: −
D. 16S rDNA Sequence
  (1) Sequence information: SEQ ID NO: 1
  (2) Molecular phylogenetic analysis: attributed to *Bacillus methylotrophicus*

The bacteriological properties of FET-037 are shown below.

A. Morphological Properties
  (1) Cell size: 1.8×0.8 μm
  (2) Cell shape: rod
  (3) Motility: +
  (4) Spores: +
B. Culture Properties
  (1) Nutrient agar medium
    (a) Colony color: milky white
    (b) Colony morphology: round, shiny, rough perimeter
  (2) Nutrient gelatin medium: liquefaction
  (3) Litmus milk medium: litmus reduction, liquefaction
  (4) Growth temperature
    (a) 30° C.: +
    (b) 60° C.: −
C. Physiological properties
  (1) Gram staining: +
  (2) Aerobic or anaerobic
    (a) Aerobic
    (b) Growth under anaerobic conditions: −
  (3) Nitrate reduction: −
  (4) MR test: −
  (5) VP test: +
  (6) Production of hydrogen sulfide: −
  (7) Utilization of citric acid: −
  (8) Pigment production: −
  (9) Urease activity: +
  (10) Oxidase activity: −
  (11) Catalase activity: +
  (12) OF test: glucose fermenting bacterium
  (13) Properties by "Api 50 CHB" (trade name, Sysmex Co., Ltd.)
    (a) L-arabinose: +
    (b) D-xylose: +
    (c) D-glucose: +
    (d) D-mannose: +
    (e) D-fructose: +
    (f) D-galactose: −
    (g) Maltose: +
    (h) Sucrose: +
    (i) Lactose: −
    (j) Trehalose: +
    (k) D-sorbitol: +
    (l) D-mannitol: +
    (m) Inositol: +
    (n) Glycerol: +
    (o) Starch: +
D. 16S rDNA Sequence
  (1) Sequence information: SEQ ID NO: 2
  (2) Molecular phylogenetic analysis: attributed to *Bacillus* sp. closely related to *Bacillus subtilis*

The microorganisms explained above can be cultured, stored, have the cells separated, and the like by methods commonly used for *Bacillus*. For example, culture can be carried out by nutrient medium (0.3% meat extract, 0.5% peptone) or LB medium (0.5% yeast extract, 1% peptone, 1% sodium chloride), or the like, to give examples of nutrient media.

Embodiments of the present invention are explained below with reference to the drawings.

Figure 1:
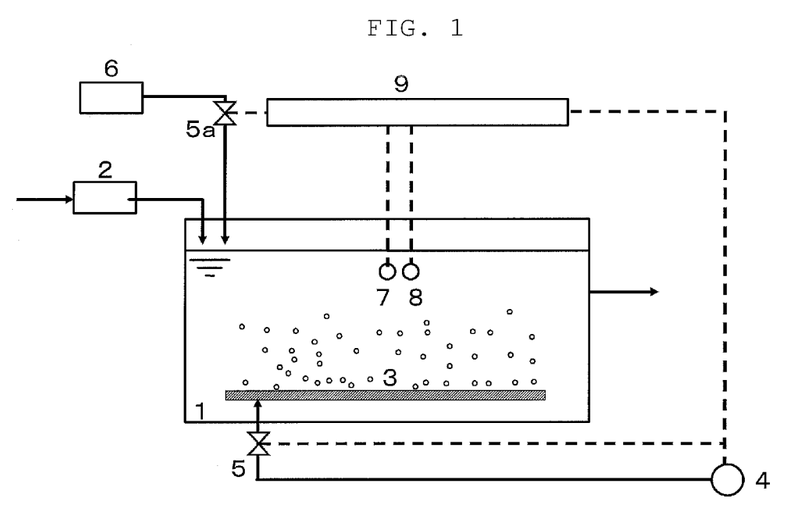
FIG. 1 is a schematic diagram showing an example of a biological treatment apparatus for implementing the wastewater treatment method of the present invention.

FIG. 1 is a schematic diagram showing an example of a biological treatment apparatus for implementing the wastewater treatment method of the present invention. This biological treatment apparatus is provided with a biological treatment tank 1 for biological treatment of wastewater, a flow rate regulation tank 2 for regulating the influx of wastewater into the biological treatment tank 1, and an air diffuser 3 at the bottom of the biological treatment tank 1. Air is supplied to the air diffuser 3 from a blower 4 via a valve 5, making it possible to aerate the wastewater being treated in the biological treatment tank 1. An activating agent is also supplied, to improve the activity of the *Bacillus*, from an activating agent supply tank 6 via a valve 5a. A hydrogen ion concentration meter (pH meter) 7 and an oxidation-reduction potentiometer (ORP meter) 8 are also provided to measure the water quality inside the biological treatment tank 1. The values measured by the hydrogen ion concentration meter (pH meter) 7 and oxidation-reduction potentiometer (ORP meter) 8 are calculated inside a control unit 9, making it possible to control the blower 4 and valve 5 (aeration ON/OFF, or aeration air volume adjustment) to provide appropriate aeration and to control the supply of activating agent from the activating agent supply tank 6 (supply ON/OFF, or supply volume adjustment). Wastewater that has been treated for a predetermined length of time inside the biological treatment tank 1 is sent to a settling tank (not shown in the diagram) for solid-liquid separation, and the solid portion is subjected to waste treatment as excess sludge or sent back to the biological treatment tank 1 to be reused as activated sludge. The liquid portion is released directly or after being brought to a water quality that meets wastewater standards if necessary.

In the present invention, the first microorganism belonging to the genus *Bacillus* that is + for nitric acid reduction and − for starch decomposition and the second microorganism belonging to the genus *Bacillus* that is − for nitric acid reduction and + for starch decomposition are made to predominate inside this biological treatment tank 1. "Predominate" means that their numbers are predominant among the biota living in the biological treatment tank 1. Whether or not they are predominant can be ascertained by randomly identifying the biota living inside the biological treatment tank 1, determining the proportion of microorganisms belonging to the genus *Bacillus* to those of other species, and determining the proportion of *Bacillus* having the above properties contained among these *Bacillus* by testing the physiological properties of the microorganisms, or the like. Specifically, the number of the first microorganism and the second microorganism present per mL of sludge in the biological treatment tank 1 should be about $1 \times 10^7$-$1 \times 10^{10}$ cells each.

The means for causing the first microorganism and the second microorganism to be predominant in the biological treatment tank 1 is not particularly restricted, and examples of methods of maintaining treatment conditions that maintain these *Bacillus* include adding *Bacillus* having the above properties to the wastewater before it enters the biological treatment tank 1, adding them to the wastewater after it has entered the biological treatment tank 1, or adding them to the activated sludge sent back from the settling tank, or the like. Specifically, adding these microorganisms at an early stage in wastewater treatment can ensure that their numbers are predominant among the biota living inside the biological treatment tank 1, creating a situation in which *Bacillus* having the above properties predominate during the treatment period as long as the treatment conditions are maintained subsequently by the usual methods. Alternatively, a method may be used whereby excess sludge obtained after conducting wastewater treatment by causing *Bacillus* having the above properties to predominate, which contains many spores, etc. of these *Bacillus*, is added to wastewater to be newly treated, and treatment conditions subsequently are maintained to maintain the *Bacillus*. These means of predomination can be incorporated easily even into conventional wastewater treatment systems.

The wastewater treatment conditions can be in accordance with the usual methods. Typically, for example, the concentration of activated sludge (MLSS) in the treated wastewater inside the biological treatment tank 1 is regulated to the 2000 mg/L-2500 mg/L range and the pH is close to neutral, preferably regulated to the 6.5-7 range. Treatments for utilizing the activity of microorganisms that tend to prefer anaerobic conditions (denitrifying bacteria, dephosphorizing bacteria, denitrifying phosphorus-accumulating bacteria, and the like) and treatments for utilizing the activity of microorganisms that tend to prefer aerobic conditions (nitrifying bacteria, yeasts, *Escherichia coli*, and the like) may be carried out in a stepwise manner, continuously, or intermittently inside the biological treatment tank 1. Although it also depends on the nitrogen concentration, phosphorus concentration, etc. in the wastewater, the oxidation-reduction potential under anaerobic conditions in this case is preferably regulated to the −150 mV to −200 mV range, and dissolved oxygen under aerobic conditions is preferably regulated to the 2.0 mg/L-3.5 mg/L range. For example, this can be done by adjusting the supply of air from the air diffuser 3 in the biological treatment apparatus shown in FIG. 1. However, it is preferable to conduct, in an end step, treatment by aerobic conditions under which nitrifying bacteria act so that no ammonia, which is an odoriferous component, remains in the wastewater that has been treated for a predetermined period of time inside the biological treatment tank 1, and to end treatment inside the biological treatment tank 1.

In the present invention, an activating agent may be added to the wastewater to be treated in the biological treatment tank 1 to maintain treatment conditions that maintain *Bacillus* or to improve the activity of the *Bacillus*. For example, the supply of activating agent from the activating agent supply tank 6 can be adjusted in the biological treatment apparatus shown in FIG. 1. An example of an activating agent is minerals containing silicic acid; specific examples include silicates, iron salts, magnesium salts, calcium salts, aluminum salts, titanium salts, and the like. It is especially preferable from the viewpoint of the growth of *Bacillus* to add an activating agent in correspondence to the organic matter concentration in the wastewater to promote the growth of *Bacillus* and to maintain the treatment capacity when the organic matter concentration is elevated in the wastewater to be treated in the biological treatment tank 1.

Figure 2:
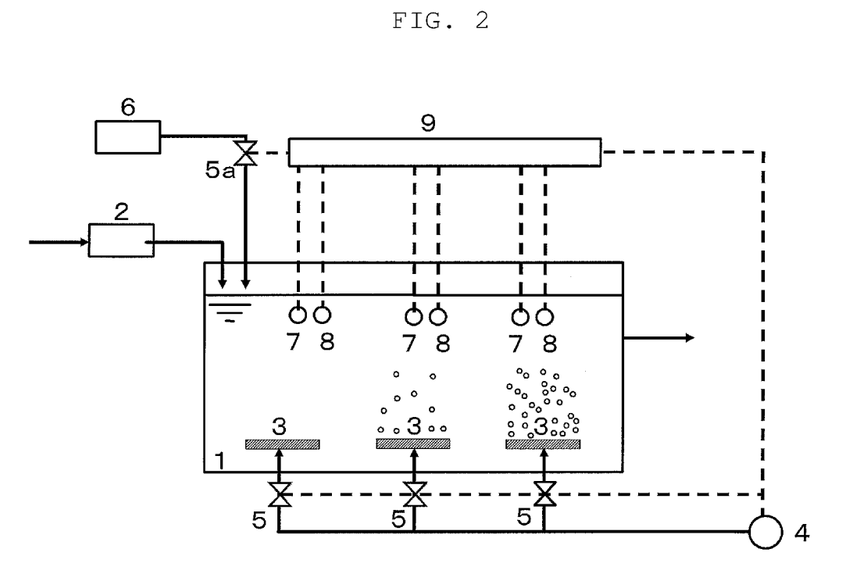
FIG. 2 is a schematic diagram showing another example of a biological treatment apparatus for implementing the wastewater treatment method of the present invention.

FIG. 2 is a schematic diagram showing another example of a biological treatment apparatus for implementing the wastewater treatment method of the present invention. This biological treatment apparatus differs from the biological treatment apparatus shown in FIG. 1 in that multiple (three in FIG. 2) air diffusers 3 are provided at the bottom of the biological treatment tank 1. In this way, air is supplied to the air diffusers 3 from a blower 4 via a valve 5, and the amount of air diffused is adjusted so as to gradually increase from the side where the wastewater is supplied (left side in FIG. 2, referred to hereinafter as the "wastewater supply side") toward the side where the wastewater is discharged (right side in FIG. 2, referred to hereinafter as "wastewater discharge side"), so as to continuously form an anaerobic region and aerobic region inside the biological treatment tank 1. In addition, the wastewater inside the biological treatment tank 1 flows slowly from the wastewater supply side toward the wastewater discharge side by a gradient of the amount of air diffused from the air diffusers 3 and/or a stirring apparatus (not shown in the drawing).

Therefore, the wastewater that has entered the biological treatment tank 1 is first exposed to anaerobic conditions in an anaerobic region inside the biological treatment tank 1, after a predetermined period of time, it is exposed to aerobic conditions for a predetermined period of time in an aerobic region inside the biological treatment tank 1. This makes it possible to efficiently conduct treatment for utilizing the activity of microorganisms that tend to prefer anaerobic conditions (denitrifying bacteria, dephosphorizing bacteria, denitrifying phosphorus-accumulating bacteria, and the like) and treatment for utilizing the activity of microorganisms that tend to prefer aerobic conditions (nitrifying bacteria, yeasts, *Escherichia coli*, and the like) inside the biological treatment tank 1.

EXAMPLES

The present invention is explained more concretely below through examples, but the scope of the present invention is in no way limited by these examples.

Comparative Example 1

Using the biological treatment apparatus discussed above shown by the schematic diagram in FIG. 1, 1 L of sewage water sample was introduced into the biological treatment tank 1 (capacity 2 L), ordinary activated sludge was added, and batch processing was conducted for ten days while aerating. Aeration was controlled (ON/OFF and aeration flow rate) during this time so that the hydrogen ion concentration (pH) was close to neutral, specifically from 6.5 to 7.

Example 1

Wastewater treatment was conducted in the same way as in Comparative Example 1 except that FET-008 and FET-037 were each added to make counts of about $1 \times 10^8$ cells/mL to 1 L of sewage water sample before beginning treatment.

[Evaluation]

The inside of the biological treatment tank 1 was uniformly mixed on days 0, 2, 4, 8, and 10 after the start of processing, and 50 mL of the processing solution was sampled. The solids were collected by natural sedimentation (centrifugation), and their dry weight was measured. The volume of sludge generated in the biological treatment tank was calculated from this value, and taken as the cumulative volume of sludge generated. The results are shown in FIG. 3.

Figure 4:
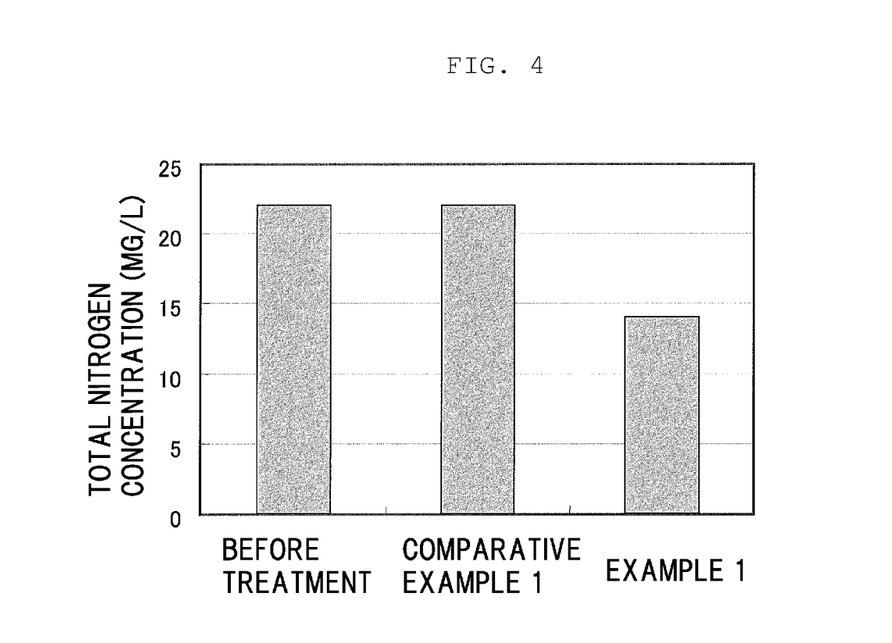
FIG. 4 is a diagram showing the results obtained by comparing the total nitrogen concentration in the treated water in the method of Example 1 and the method of Comparative Example 1.

The total nitrogen concentration of the treated water (liquid portion from which the solids had been removed by natural sedimentation) after the end of processing was also measured by absorption photometry (JIS K 0102 45.2), and compared with the total nitrogen concentration of the wastewater before the start of processing. The results are shown in FIG. 4.

Figure 3:
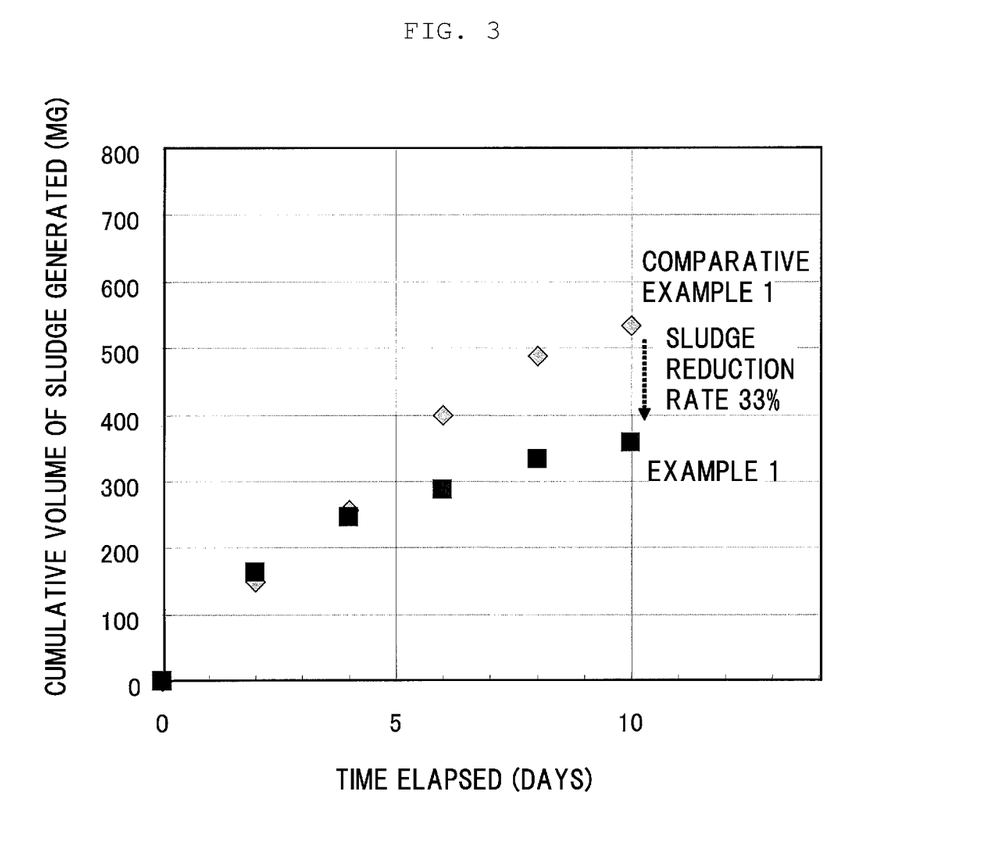
FIG. 3 is a diagram showing the results obtained by comparing the cumulative volume of sludge generated in the method of Example 1 and the method of Comparative Example 1.

As shown in FIG. 3, a sludge reduction effect of 33% was seen in Example 1 that used FET-008 and FET-037 in comparison to Comparative Example 1 that used a conventional processing method. In addition, as shown in FIG. 4, the total nitrogen concentration of the wastewater before processing of 22 mg/L fell to 14 mg/L after processing in Example 1, in which FET-008 and FET-037 were used, for a high nitrogen removal rate of 46%, in contrast to Comparative Example 1 that used a conventional processing method where virtually no nitrogen was removed.

The above clarifies that purifying wastewater using FET-008 and FET-037 makes it possible to improve the water quality of the treated water by removing nitrogen in the wastewater while suppressing the volume of sludge generated in association with wastewater treatment.

Test Example 1

The starch decomposition activity of FET-008 and FET-037 was studied.

To this end, nutrient medium was inoculated with FET-008 or FET-037, and they were cultured overnight at 30° C.

Cultures having "Power UP A" (trade name, Taisei Kigyo Corp.) added to make 2 mg/mL as a mineral to improve the activity of the *Bacillus* were also cultured in the same way. The starch decomposing activity secreted in the culture broth was compared by a coloring reaction by iodine starch reaction.

Specifically, the culture broth was filtered through a filter having a pore size of 0.2 μm, and 3 mL of 0.5% water-soluble starch was added to 1 mL of the filtrate. After 60 minutes, iodine solution was added dropwise. If starch remains, the solution turns the purple characteristic of the iodine starch reaction; if the starch has been decomposed, it does not change color. The coloration was measured at an absorbance of 550 nm.

Figure 5:
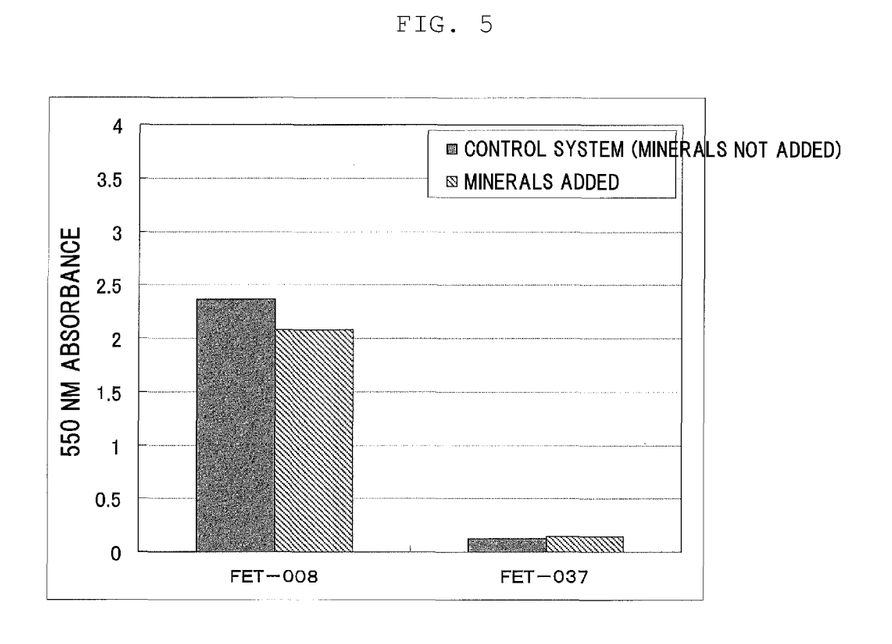
FIG. 5 is a diagram showing the results obtained by measuring the coloration of an iodine starch reaction in Test Example 1 based on the 550 nm absorbance.

As shown in FIG. 5, the results clarified that, regardless of whether or not minerals were added, the added starch disappeared and the starch decomposing activity was high in FET-037. In contrast, the added starch remained, and the starch decomposing activity was weak, regardless of whether or not minerals were added, in FET-008. These results are consistent with the properties regarding "starch" obtained by "Api 50 CHB" (trade name, Sysmex Co., Ltd.) in the bacteriological testing discussed above.

Test Example 2

The proteolytic activity of FET-008 and FET-037 was studied.

Specifically, culture broth filtrate prepared in the same way as in Test Example 1 was supplied to a fluorescent proteolytic enzyme assay kit (Thermo Fisher Scientific, Inc.), and the proteolytic activity secreted in the culture broth was measured. This kit shows a rise in fluorescence intensity due to the presence of proteolytic enzymes, and the proteolytic enzyme activity per unit cell concentration was compared by dividing the measured fluorescence intensity by the 600 nm absorbance that represents the cell concentration.

Figure 6:
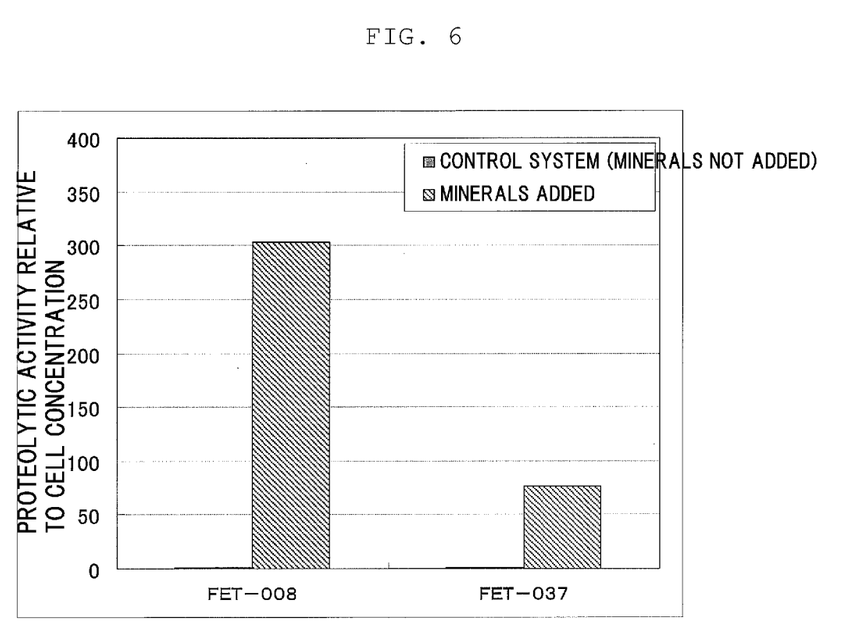
FIG. 6 is a diagram showing the results on protein decomposition activity relative to cell concentration measured in Test Example 2.

As shown in FIG. 6, the proteolytic activity in the culture broth was below the lower limit of detection in both FET-008 and FET-037 when no minerals were added. When minerals were added, however, proteolytic activity was found. This activity was higher with FET-008 than FET-037.

Furthermore, when casein, a water-insoluble milk protein, was added to the culture broth after culture as a check, dissolution of the casein was observed, and lowering of the molecular weight due to proteolytic enzymes was demonstrated.

The results of Test Example 1 and Test Example 2 above showed that FET-008 and FET-037 have the ability to decompose organic matter in wastewater, in particular that FET-008 is superior in its ability to decompose protein and that FET-037 is superior in its ability to decompose starch, and that the use of these *Bacillus* can purify wastewater as well as reduce the volume of sludge generated.

Test Example 3

The nitrogen source assimilation characteristics of FET-008 and FET-037 were studied.

First, nutrient medium was inoculated with FET-008 or FET-037, and they were cultured overnight at 30° C. The cells were collected by centrifugation, washed and resuspended by phosphate-buffered physiological saline, and the medium components were eliminated.

On the other hand, minimal medium of the composition shown below in Table 1 was prepared by modifying *Bacillus* subtilis minimal medium and adding ammoniacal nitrogen or nitrate-nitrogen as a nitrogen source.

TABLE 1

| | |
|---|---|
| Dipotassium hydrogen phosphate | 14 g |
| Potassium dihydrogen phosphate | 6 g |
| Sodium citrate dihydrate | 1 g |
| Magnesium sulfate heptahydrate | 0.25 g |
| Glucose | 5 g |
| Nitrogen source: ammonium chloride or sodium nitrate | 1 g |
| Pure water | 1 L |

This minimal medium was inoculated with the above cell suspension and shake cultured for five days at 30° C. under aerobic conditions or anaerobic conditions.

After culture, bacterial growth was compared by measuring the OD 600. The presence of nitrite-nitrogen and nitrate-nitrogen in the medium was also detected using Griess-Romijn's nitrite detection reagent and Griess-Romijn's nitrate detection reagent (Wako Pure Chemical Industries, Ltd.), and the presence of ammoniacal nitrogen was detected using the pack test (Kyoritsu Institute of Physical and Chemical Research, Inc.). The results on FET-008 are shown in FIG. 7 and Table 2, and those on FET-037 are shown in FIG. 8 and Table 3.

[Evaluation of FET-008]

Figure 7:
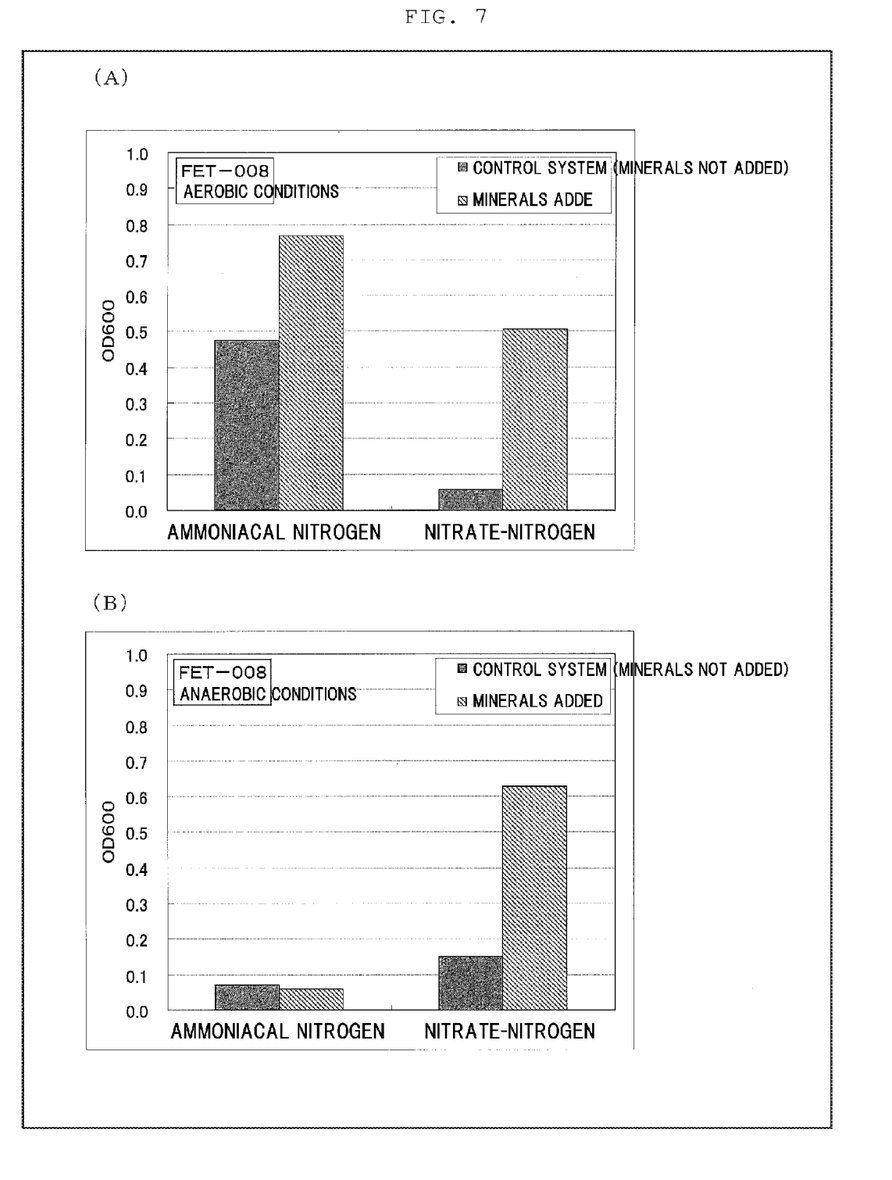
FIG. 7 is a diagram showing the results obtained by studying the nitrogen source assimilation characteristics of FET-008 in Test Example 3. (A) is a diagram showing the results under aerobic conditions; (B) is a diagram showing the results under anaerobic conditions.
Figure 8:
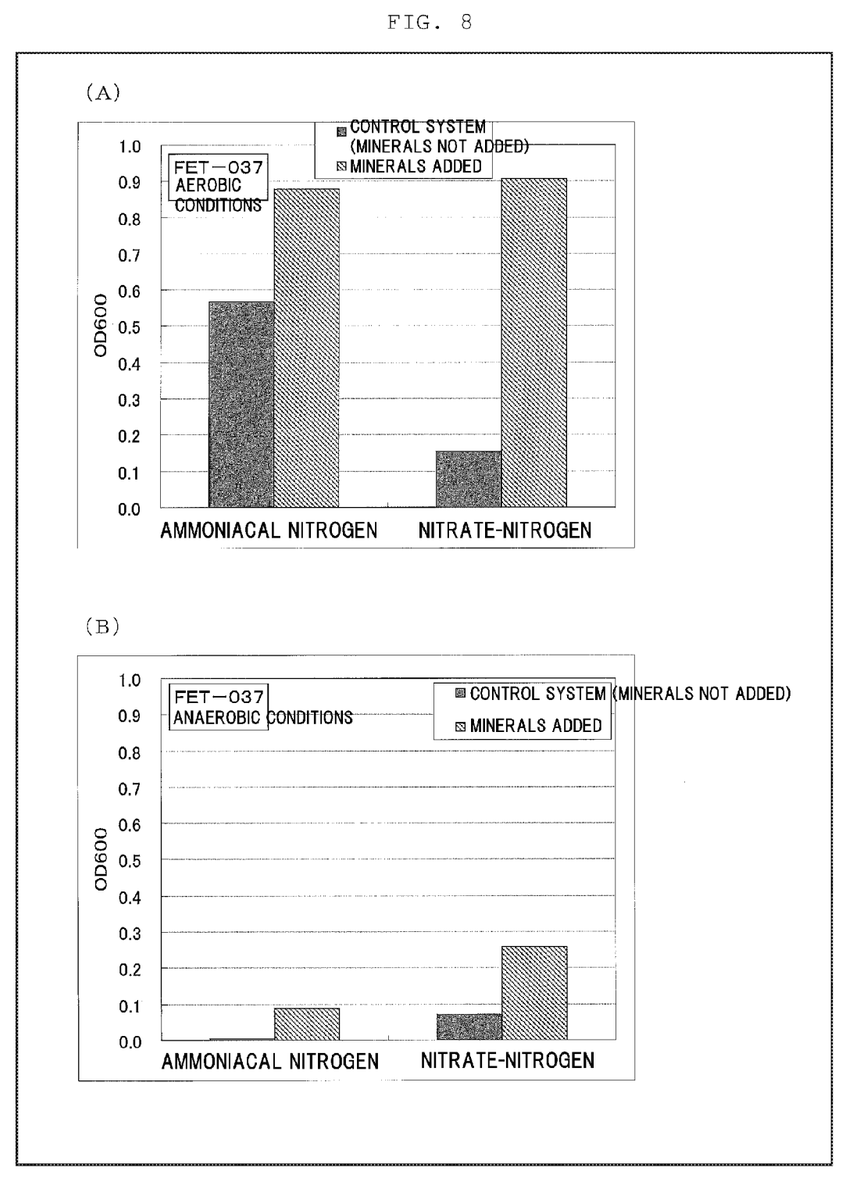
FIG. 8 is a diagram showing the results obtained by studying the nitrogen source assimilation characteristics of FET-037 in Test Example 3. (A) is a diagram showing the results under aerobic conditions; (B) is a diagram showing the results under anaerobic conditions.

As shown in FIGS. 7A and B, FET-008 grew by assimilating ammoniacal nitrogen, regardless of whether minerals were added or not, when cultured under aerobic conditions with ammoniacal nitrogen as a nitrogen source. On the other hand, FET-008 could assimilate virtually no ammoniacal nitrogen and did not grow, regardless of whether minerals were added or not, when cultured under anaerobic conditions. This shows that the bacteria assimilate ammonia and reproduce and grow in systems having ammoniacal nitrogen as a nitrogen source, but this ammonia assimilation is strongly dependent on oxygen in FET-008.

In contrast, as regards the assimilation of nitrate-nitrogen by FET-008, very slight bacterial growth was found but virtually no nitrate-nitrogen could be assimilated under aerobic conditions, and the bacteria did not grow at all under anaerobic conditions when no minerals were added. On the other hand, when minerals were added, bacterial growth was seen under both aerobic and anaerobic conditions. This shows that both the nitrate reduction reaction under aerobic conditions and the nitrate reduction reaction under anaerobic conditions are activated by minerals, and ammonia assimilation occurs after nitric acid has been reduced to ammonia. It is also suggested that the ammonia assimilation reaction under anaerobic conditions requires nitric acid in addition to minerals.

Table 2 shows the residual state of nitrogen components in the medium after culture.

TABLE 2

| FET-008 | Nitrogen source | Minerals | $NH_4$ | $NO_2$ | $NO_3$ |
|---|---|---|---|---|---|
| Aerobic conditions | Ammoniacal nitrogen | Not added | – | – | |
| | | Added | – | – | |
| | Nitrate-nitrogen | Not added | ± | + | |
| | | Added | ± | + | |
| Anaerobic conditions | Ammoniacal nitrogen | Not added | – | – | – |
| | | Added | – | – | |
| | Nitrate-nitrogen | Not added | ± | + | |
| | | Added | + | + | |

As shown in Table 2, production of nitrous acid and ammonia was confirmed in a system having nitrate-nitrogen as the nitrogen source under aerobic conditions. This shows that nitrate-nitrogen is reduced to ammonia via nitrous acid. It is also understood that the nitric acid reduction is reinforced by the addition of minerals under anaerobic conditions.

[Evaluation of FET-037]

As shown in FIGS. 8A and B, FET-037 assimilated ammoniacal nitrogen and grew, regardless of whether minerals were added or not, when cultured under aerobic conditions with ammoniacal nitrogen as the nitrogen source. On the other hand, when FET-037 was cultured under anaerobic conditions, the bacteria assimilated virtually no ammoniacal nitrogen and did not grow, regardless of whether minerals were added or not. This shows that the bacteria assimilate ammonia and reproduce and grow in systems having ammoniacal nitrogen as a nitrogen source, but this ammonia assimilation is strongly dependent on oxygen in FET-037.

In contrast, as regards the assimilation of nitrate-nitrogen by FET-037, very slight bacterial growth was found but virtually no nitrate-nitrogen could be assimilated under aerobic conditions, and the bacteria did not grow at all under anaerobic conditions when no minerals were added. On the other hand, when minerals were added, bacterial growth was seen under both aerobic and anaerobic conditions. This shows that both the nitrate reduction reaction under aerobic conditions and the nitrate reduction reaction under anaerobic conditions are activated by minerals, and ammonia assimilation occurs after nitric acid has been reduced to ammonia. It is also suggested that the ammonia assimilation reaction under anaerobic conditions requires nitric acid in addition to minerals.

Table 3 shows the residual state of nitrogen components in the medium after culture.

TABLE 3

| FET-037 | Nitrogen source | Minerals | $NH_4$ | $NO_2$ | $NO_3$ |
|---|---|---|---|---|---|
| Aerobic conditions | Ammoniacal nitrogen | Not added | – | – | |
| | | Added | – | – | |
| | Nitrate-nitrogen | Not added | ± | + | |
| | | Added | ± | – | |
| Anaerobic conditions | Ammoniacal nitrogen | Not added | – | – | |
| | | Added | – | – | |
| | Nitrate-nitrogen | Not added | + | + | |
| | | Added | + | + | |

As shown in Table 3, production of nitrous acid and ammonia was confirmed in a system having nitrate-nitrogen as the nitrogen source under aerobic conditions. This shows that nitrate-nitrogen is reduced to ammonia via nitrous acid. It is also understood that the nitric acid reduction is reinforced by the addition of minerals under anaerobic conditions.

EXPLANATION OF NUMERALS AND CHARACTERS

1: Biological treatment tank
2: Flow rate regulation tank
3: Air diffuser
4: Blower
5, 5a: Valve
6: Activating agent supply tank
7: Hydrogen ion concentration meter (pH meter)

8: Oxidation-reduction potentiometer (ORP meter)
9: Control unit
PCT

| | | |
|---|---|---|
| 0-1 | Form PCT/RO/134 (SAFE) Identifiers relating to these deposited microorganisms or other biological materials (PCT rule 13.2) were created as stated to the right. | |
| 0-1-1 | | JPO-PAS i222 |
| 0-2 | International Application No. | |
| 0-3 | Document symbol of applicant or agent | 12P50479WO |
| 1 | The following identifier is related to microorganisms or biological materials discussed in the patent specification. | |
| 1-1 | Paragraph number | 29 |
| 1-3 | Display of deposit | |
| 1-3-1 | Name of depositary | NPMD National Institute of Technology and Evaluation Patent Microorganisms Depositary (NPMD) |
| 1-3-2 | Depositary address | 2-5-8 Kazusakamatari, Kisarazu-shi, Chiba 292-0818, Japan |
| 1-3-3 | Date of deposit | Oct. 12, 2012 |
| 1-3-4 | Accession number | NPMD NITE BP-1426 |
| 1-5 | Designated states for this display | All designated states |
| 2 | The following display is related to microorganisms or biological materials discussed in the patent specification. | |
| 2-1 | Paragraph number | 30 |
| 2-3 | Display of deposit | |
| 2-3-1 | Name of depositary | NPMD National Institute of Technology and Evaluation Patent Microorganisms Depositary (NPMD) |
| 2-3-2 | Depositary address | 2-5-8 Kazusakamatari, Kisarazu-shi, Chiba 292-0818, Japan |
| 2-3-3 | Date of deposit | Oct. 12, 2012 |
| 2-3-4 | Accession number | NPMD NITE BP-1427 |
| 5-5 | Designated states for this display | All designated states |

For Receiving Office Use

| | | |
|---|---|---|
| 0-4 | This paper was received together with the international application (yes/no) | |
| 0-4-1 | Authorized employee | |

For World International Patent Office Use

| | | |
|---|---|---|
| 0-5 | Date this paper was received by the World International Patent Office | |
| 0-5-1 | Authorized employee | |

The invention claimed is:

1. A method for purifying a wastewater containing living biota comprising:
   (a) introducing a wastewater into a biological treatment tank in which anaerobic conditions and aerobic conditions are maintained;
   (b) introducing a first microorganism and a second microorganism into the biological treatment tank either before or after the introduction of the wastewater into the biological treatment tank, wherein the first microorganism belongs to *Bacillus methylotrophicus* and the second microorganism belongs to *Bacillus subtilis*, and wherein the first microorganism and the second microorganism predominate over said living biota in the biological treatment tank; and
   (c) introducing at least one activating agent comprising silicic acid into the biological treatment tank.

2. The method according to claim 1, wherein the first microorganism and the second microorganism both have a higher ability to grow in aerobic conditions with ammoniacal nitrogen as a nitrogen source when compared to growth in anaerobic conditions with ammoniacal nitrogen as a nitrogen source in testing with a liquid medium.

3. The method according to claim 1, wherein the first microorganism is a microorganism having a 16S rDNA sequence of SEQ ID NO: 1.

4. The method according to claim 3, wherein the first microorganism is *Bacillus* methylotrophicus FET-008 (accession number: NITE BP-1426) belonging to the genus *Bacillus*.

5. The method according to claim 1, wherein the second microorganism is a microorganism having a 16S rDNA sequence of SEQ ID NO: 2.

6. The method according to claim 5, wherein the second microorganism is *Bacillus* sp. FET-037 (accession number: NITE BP-1427) belonging to the genus *Bacillus*.

7. The method according to claim 1, wherein:
   the first microorganism has a higher ability in nitrate-nitrogen reduction and protein decomposition than the second microorganism in testing with a liquid medium in anaerobic conditions, and
   the second microorganism has a higher ability in nitrate-nitrogen reduction and protein decomposition than the first microorganism in testing with a liquid medium in aerobic conditions.

* * * * *

UNITED STATES PATENT AND TRADEMARK OFFICE
CERTIFICATE OF CORRECTION

PATENT NO. : 9,994,469 B2
APPLICATION NO. : 15/116054
DATED : June 12, 2018
INVENTOR(S) : Kazuyuki Taguchi et al.

Page 1 of 1

It is certified that error appears in the above-identified patent and that said Letters Patent is hereby corrected as shown below:

On the Title Page

Column 1, Line 3, item (*) Notice, after "0 days." delete "days.".

In the Drawings

Sheet 7 of 8, FIG. 7, Line 4, delete "ADDE" and insert --ADDED--.

Signed and Sealed this
Sixteenth Day of October, 2018

Andrei Iancu
*Director of the United States Patent and Trademark Office*

SEQUENCE LISTING

<160> NUMBER OF SEQ ID NOS: 2

<210> SEQ ID NO 1
<211> LENGTH: 765
<212> TYPE: DNA
<213> ORGANISM: Bacillus methylotrophicus

<400> SEQUENCE: 1

```
ggacgaacgc tggcggcgtg cctaatacat gcaagtcgag cggacagatg ggagcttgct      60
ccctgatgtt agcggcggac gggtgagtaa cacgtgggta acctgcctgt aagactggga     120
taactccggg aaaccgggc  taataccgga tggttgtttg aaccgcatgg ttcagacata     180
aaaggtggct tcggctacca cttacagatg gacccgcggc gcattagcta gttggtgagg     240
taacggctca ccaaggcgac gatgcgtagc cgacctgaga gggtgatcgg ccacactggg     300
actgagacac ggcccagact cctacgggag gcagcagtag ggaatcttcc gcaatggacg     360
aaagtctgac ggagcaacgc cgcgtgagtg atgaaggttt tcggatcgta aagctctgtt     420
gttagggaag aacaagtgcc gttcaaatag ggcggcacct tgacggtacc taaccagaaa     480
gccacggcta actacgtgcc agcagccgcg gtaatacgta ggtggcaagc gttgtccgga     540
attattgggc gtaaagggct cgcaggcggt ttcttaagtc tgatgtgaaa gccccggct     600 caaccgggga gggtcattgg aaactgggga acttgagtgc agaagaggag agtggaattc     660
cacgtgtagc ggtgaaatgc gtagagatgt ggaggaacac cagtggcgaa ggcgactctc     720
tggtctgtaa ctgacgctga ggagcgaaag cgtgggagc  gaaca                    765
```

<210> SEQ ID NO 2
<211> LENGTH: 765
<212> TYPE: DNA

```
<213> ORGANISM: Bacillus sp.

<400> SEQUENCE: 2
ggacgaacgc tggcggcgtg cctaatacat gcaagtcgag cggacagatg ggagcttgct      60
ccctgatgtt agcggcggac gggtgagtaa cacgtgggta acctgcctgt aagactggga     120
taactccggg aaaccggggc taataccgga tggttgtttg aaccgcatgg ttcaaacata     180
aaaggtggct tcggctacca cttacagatg gacccgcggc gcattagcta gttggtgagg     240
taacggctca ccaaggcgac gatgcgtagc cgacctgaga gggtgatcgg ccacactggg     300
actgagacac ggcccagact cctacgggag gcagcagtag ggaatcttcc gcaatggacg     360
aaagtctgac ggagcaacgc cgcgtgagtg atgaaggttt tcggatcgta aagctctgtt     420
gttagggaag aacaagtacc gttcgaatag ggcggtacct tgacggtacc taaccagaaa     480
gccacggcta actacgtgcc agcagccgcg gtaatacgta ggtggcaagc gttgtccgga     540
attattgggc gtaaagggct cgcaggcggt ttcttaagtc tgatgtgaaa gcccccggct     600
caaccgggga gggtcattgg aaactgggga acttgagtgc agaagaggag agtggaattc     660
cacgtgtagc ggtgaaatgc gtagagatgt ggaggaacac cagtggcgaa ggcgactctc     720
tggtctgtaa ctgacgctga ggagcgaaag cgtgggagc gaaca                     765
```